United States Patent
Terasaki et al.

(10) Patent No.: US 9,944,979 B2
(45) Date of Patent: Apr. 17, 2018

(54) INHIBITION METHOD OF NUCLEIC ACID AMPLIFICATION BY PHOTOIRRADIATION AND METHOD OF SELECTIVE NUCLEIC ACID AMPLIFICATION WITH HIGH SENSITIVITY

(75) Inventors: Hiroshi Terasaki, Tokyo (JP); Tsunetada Konno, Tokyo (JP); Mitsunobu Shimadzu, Tokyo (JP); Kenzo Fujimoto, Ishikawa (JP); Takashi Sakamoto, Ishikawa (JP)

(73) Assignee: LSI MEDIENCE CORPORATION, Tokyo (JP)

( * ) Notice: Subject to any disclaimer, the term of this patent is extended or adjusted under 35 U.S.C. 154(b) by 5 days.

(21) Appl. No.: 13/821,968

(22) PCT Filed: Sep. 9, 2011

(86) PCT No.: PCT/JP2011/070579
§ 371 (c)(1),
(2), (4) Date: Mar. 8, 2013

(87) PCT Pub. No.: WO2012/033190
PCT Pub. Date: Mar. 15, 2012

(65) Prior Publication Data
US 2013/0177918 A1  Jul. 11, 2013

(30) Foreign Application Priority Data
Sep. 10, 2010 (JP) ................. 2010-203054

(51) Int. Cl.
 *C12Q 1/68* (2006.01)
(52) U.S. Cl.
 CPC ........... *C12Q 1/686* (2013.01); *C12Q 1/6858* (2013.01)

(58) Field of Classification Search
None
See application file for complete search history.

(56) References Cited

U.S. PATENT DOCUMENTS

2009/0053720 A1* 2/2009 Newton ............... C12Q 1/6858
  435/5
2009/0221429 A1 9/2009 Fujimoto et al.
(Continued)

FOREIGN PATENT DOCUMENTS

| | | |
|---|---|---|
| JP | 4216266 B2 | 10/2006 |
| JP | 2009-213445 | 9/2009 |

(Continued)

OTHER PUBLICATIONS

Sotlar et al. (2003) Am. J. Pathol vol. 162:737-746.*
(Continued)

*Primary Examiner* — Suchira Pande
(74) *Attorney, Agent, or Firm* — Kilpatrick Townsend & Stockton LLP

(57) ABSTRACT

Provided is a method for rapidly and easily detecting a mutated nucleic acid, which is contained in a small amount in a nucleic acid sample together with wild-type nucleic acids, with high specificity and high sensitivity. In the method of the present invention, amplification of a detection region comprising a target site by a nucleic acid amplification method is inhibited, by the steps of allowing a nucleic acid having a target site to coexist with a clamp probe comprising a photo-crosslinking nucleic acid and having a sequence complementary to the target site, and photo-crosslinking the nucleic acid having the target site with the clamp probe by photo-irradiation.

8 Claims, 4 Drawing Sheets

(56) References Cited

U.S. PATENT DOCUMENTS

| | | | |
|---|---|---|---|
| 2010/0009355 A1 | 1/2010 | Kolodney | |
| 2010/0274000 A1 | 10/2010 | Fujimoto et al. | |
| 2011/0034683 A1 | 2/2011 | Fujimoto et al. | |

FOREIGN PATENT DOCUMENTS

| | | |
|---|---|---|
| JP | 2010-158178 | 7/2010 |
| WO | 03/095680 A1 | 11/2003 |
| WO | 2005/072133 A2 | 8/2005 |
| WO | 2006/102569 A2 | 9/2006 |
| WO | WO 2009/083763 A1 | 7/2009 |

OTHER PUBLICATIONS

Pieles et al., "Preparation of a novel psoralen containing deoxyadenosine building block for the facile solid phase synthesis of psoralen-modified oligonucleotide for a sequence specific cross-link to a given target sequence," Nucleic Acids Research, 1989, vol. 17, No. 22, pp. 8967-8978.*

Yoshimura and Fujimoto; Ultrafast Reversible Photo-Cross-Linking Reaction: Toward in Situ DNA Manipulation; Organic Letters; 2008; vol. 10, No. 15, pp. 3227-3230.

Yoshimura, et al; SNP genotyping by DNA photoligation: application to SNP detection of genes from food crops; Science and Tech of Adv. Materials; Jul. 2009; vol. 10, p. 034603.

Ami, et al; Sequence specific interstrand photocrosslinking for effective SNP typing; Organic & Biomolecular Chem.; 2007; vol. 5, pp. 2583-2586.

Yoshimura, et al; Interstrand photocrosslinking of DNA via p-carbamoylvinyl phenol nucleoside; Bioorganic & Medicinal Chem.,2007, vol. 15, pp. 1299-1301.

International Search Report from PCT/JP2011/070579 dated Oct. 6, 2011.

Qiagen: "Sample & Assay Technologies Q-Pure Detection," Rotor-Gene Q-Pure Detection, Mar. 1, 2010, pp. 1-16.

EP application No. 11 82 3664, Supplementary European Search Report, dated Dec. 17, 2013, 2 pages.

\* cited by examiner

| 1 Wild-type ODN (−), Photoirradiation (−) | CP value 9.2 |
| 2 Wild-type ODN (−), Photoirradiation (+) | CP value 9.1 |
| 3 Wild-type ODN (+), Photoirradiation (−) | CP value 9.0 |
| 4 Wild-type ODN (+), Photoirradiation (+) | CP value 14.1 |

| 1 Mutated-type ODN (+), Photoirradiation (−) CP value 9.3 |
| 2 Mutated-type ODN (+), Photoirradiation (+) CP value 9.6 |

SEQUENCE LISTING

```
<160> NUMBER OF SEQ ID NOS: 12

<210> SEQ ID NO 1
<211> LENGTH: 22
<212> TYPE: DNA
<213> ORGANISM: Homo sapiens

<400> SEQUENCE: 1
aaaggtactg gtggagtatt tg                                              22

<210> SEQ ID NO 2
<211> LENGTH: 20
<212> TYPE: DNA
<213> ORGANISM: Homo sapiens

<400> SEQUENCE: 2
tgaaaatggt cagagaaacc                                                 20

<210> SEQ ID NO 3
<211> LENGTH: 24
<212> TYPE: DNA
<213> ORGANISM: Homo sapiens

<400> SEQUENCE: 3
aaccttatgt gtgacatgtt ctaa                                            24

<210> SEQ ID NO 4
<211> LENGTH: 20
<212> TYPE: DNA
<213> ORGANISM: Homo sapiens

<400> SEQUENCE: 4
gtcctgcacc agtaatatgc                                                 20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 5
cagggttttc ccagtcacga                                                 20
```

-continued

```
<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 6
tcacacagga aacagctatg                                              20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 7
atttaggtga cactatagaa                                              20

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 8
aatacgactc actataggg                                               19

<210> SEQ ID NO 9
<211> LENGTH: 20
<212> TYPE: DNA
<213> ORGANISM: Homo sapiens

<400> SEQUENCE: 9
gcatgaacta cttggaggac                                              20

<210> SEQ ID NO 10
<211> LENGTH: 20
<212> TYPE: DNA
<213> ORGANISM: Homo sapiens

<400> SEQUENCE: 10
acctaaagcc acctccttac                                              20

<210> SEQ ID NO 11
<211> LENGTH: 19
<212> TYPE: DNA
<213> ORGANISM: Homo sapiens

<400> SEQUENCE: 11
cttggaggac cgtcgcttg                                               19

<210> SEQ ID NO 12
<211> LENGTH: 20
<212> TYPE: DNA
<213> ORGANISM: Homo sapiens

<400> SEQUENCE: 12
ccacctcctt actttgcctc                                              20
```

INHIBITION METHOD OF NUCLEIC ACID AMPLIFICATION BY PHOTOIRRADIATION AND METHOD OF SELECTIVE NUCLEIC ACID AMPLIFICATION WITH HIGH SENSITIVITY

CROSS-REFERENCE TO RELATED APPLICATIONS

The present application is a § 371 National Phase Application of PCT/JP2011/070579, filed Sep. 9, 2011, which application claims priority to JP application 2010-203054, filed Sep. 10, 2009, the contents of both applications are hereby incorporated by reference in their entire for all purposes.

TECHNICAL FIELD

The present invention relates to a method and a kit for selectively detecting, for example, a mutated nucleic acid which coexists in a small amount together with wild-type nucleic acids using a clamp probe comprising a photo-crosslinking nucleic acid, and a nucleic acid amplification apparatus with a photo-irradiation unit at a wavelength of 350 to 380 nm.

BACKGROUND ART

After the completion of human genome sequencing, movements to utilize the obtained gene information for the medical field such as diagnosis have been activated. The next targets after the genome sequencing are gene expression profile analysis, analysis of single nucleotide substitution (Single Nucleotide Polymorphisms; SNPs) in genes, and the like. The expression levels of genes expressed under various conditions and genetic mutations have been analyzed, and the functions of genes and the relationships of genes to diseases or drug sensitivity are being revealed from the analysis, and the accumulated gene information is used for not only diagnosis of diseases but also the selection of treatment.

In particular, SNPs and mutations are important targets for genetic testing such as diagnosis of diseases or risk characterization, and used in various fields including diabetes, rheumatism, cancer, mental illness, and heart disease. As a method for detecting SNPs, various methods have been developed. Concrete examples of such methods include an invader method, a sniper method, a TaqMan PCR method, a hybridization probe method, an SNPIT method, a pyro-minisequencing method, a denaturing high performance liquid chromatography (DHPLC) method, an MALDI-TOF/MS method, and a nanochip method, as a method for rapid and high-throughput analysis.

In the field of cancer, molecular targeted drugs which target a specific molecule in the living body and suppress its function have been actively developed. Detection of single nucleotide substitution is positioned as an important test in determining the application of molecular targeted drugs when selecting treatment. For example, it is recommended to conduct mutation analysis testing for an EGFR gene or a KRAS gene before the use of anticancer drugs. This is because the presence or absence of mutation causes different drug effects, and it is guided that a drug should be administered by considering mutation. Another objective is to select a patient with a risk of severe adverse effects rather than drug efficacy and with low dosage effects by examining the presence or absence of such mutation in advance. Because of those reasons, the detection of particularly single nucleotide substitution is positioned as an important test in the field of cancer.

However, in the detection of an acquired mutation such as cancer, since wild-type nucleic acid molecules derived from normal cells which are dominant in a specimen affect as background, mutation such as single nucleotide substitution cannot be detected by analysis techniques as described above in many cases. To solve this problem, a Scorpion-ARMS method and a PNA-LNA PCR Clamping method have been developed (Patent literature 1).

The Scorpion-ARMS method is a method of analyzing a product obtained by selectively amplifying a mutated molecule using a combination of a primer designed on the basis of a mutated sequence so that the mutation point is positioned close to the 3' terminus of the primer and another primer, by a fluorescent detection method, a Scorpion method. The PNA-LNA PCR Clamping method is a method in which a wild-type molecule is selectively blocked with a clamp primer which is designed on the mutation point and is complementary to the wild-type sequence, and a mutated molecule is selectively amplified and detected using a mutated LNA as a fluorescent detection probe.

These methods utilize a difference in thermal stability in the equilibrium system of a hybrid which is formed from a primer or probe and a template molecule. The difference between hybrid formation when the primer or probe is completely complementary to the template molecule, and incomplete hybrid formation when the primer or probe is not complementary to the template molecule by one to several nucleotides is merely a difference in thermal stability. Therefore, appropriate conditions capable of distinguishing the wild-type molecule from the mutated molecule are different in accordance with the nucleotide sequence of interest, and conditions which change thermal stability equally act on both molecules even under appropriate conditions. That is to say, so long as only the difference in thermal stability of hybrid formation in the equilibrium system is utilized as the principle of the distinction between both, we have to select temperature conditions including compromise between the balance of specificity and sensitivity, and the range width of selectable temperature conditions is extremely narrow in many cases, and therefore, the design of probe and primer is often difficult for some gene sequences.

Under these circumstances of detection techniques, strict limitations are provided to collect specimens in current mutation detection testing for cancer. More particularly, it is recommended that pathological specimens are prepared from cancer tissues, the tumor site is identified from stained specimens, and only the tumor is collected from unstained specimens of serial sections (The Guidance on the measurement of KRAS gene mutations in colon cancer patients). However, the identification of the tumor site requires specialized knowledge of structural morphology, and its procedures are complicated and high cost.

Therefore, a detection method with high specificity and high sensitivity, in which there are a few limitations on the collection of specimens and the nucleotide sequence of a target gene as the requirements of testing, is desired.

As a detection method with high specificity and high sensitivity, a method for detecting a mutated gene utilizing a photo-crosslinking nucleic acid has been developed. For example, Patent literature 2 discloses a method for detecting a target nucleic acid having a specific nucleotide sequence, based on hybrid formation with a complementary chain, with high specificity and high sensitivity. In this method, a photo-crosslinking nucleic acid complementary to the target nucleic acid, and a photo-crosslinked nucleic acid having a base moiety capable of photo-crosslinking with the photo-crosslinking nucleic acid at the 3' or 5' terminus are used, and one of both nucleic acids has a label portion, and the other is immobilized on a substrate. According to this method, the photo-crosslinking nucleic acid and the photo-crosslinked nucleic acid on the same chain are specifically crosslinked with each other, utilizing photo-crosslinking, only when a complete hybrid is formed, the nucleic acid molecule with the label portion can be covalently immobilized on the substrate, complete washing can be performed under conditions where complementary double-stranded chains dissociate, and high specificity and high sensitivity are achieved.

However, the detection sensitivity in this method has a lower limit, and thus, this method can be used to detect the presence or absence of mutation contained in a large amount of target nucleic acid, but cannot be used to detect a small amount of mutated nucleic acid which coexists with a large amount of wild-type nucleic acid, because the content of the mutated nucleic acid in a small amount is less than or equal to the detection sensitivity in many cases. Further, since the photo-crosslinking nucleic acid is covalently bound to the photo-crosslinked nucleic acid on the same chain, the mutation contained in the target nucleic acid to be detected cannot be amplified.

On the other hand, Patent literature 3 discloses a method in which a sample containing a target nucleic acid is first subjected to amplification by PCR, and then the method disclosed in Patent literature 2 is performed, to detect a nucleic acid having one target nucleotide sequence or two or more target nucleotide sequences in the nucleic acid sample. When the content of the mutated nucleic acid is small, the content percentage of the wild-type nucleic acid does not change, even if the amplification by PCR can be performed, and thus, the mutated nucleic acid cannot be amplified to the detectable level by the amplification within the range detectable in vitro. Therefore, this method can be used to detect the presence or absence of mutation contained in a large amount of target nucleic acid, but cannot be used to detect a small amount of mutated nucleic acid which coexists with a large amount of wild-type nucleic acid. In addition, since a sample containing the target nucleic acid is subjected to amplification by PCR, if the content percentage of the mutated nucleic acid is higher than a certain level, there is a possibility to detect the mutated nucleic acid, but this method needs many steps and is complicated, and thus, cannot meet the demand of the clinical scene which requires rapid test results.

CITATION LIST

Patent Literature

[Patent literature 1] Japanese Patent No. 4216266
[Patent literature 2] WO2007/058326
[Patent literature 3] Japanese Unexamined Patent Publication (Kokai) No. 2009-213445

SUMMARY OF INVENTION

Technical Problem

An object of the present invention is to provide a method for rapidly and easily detecting a mutated nucleic acid, which is contained in a small amount in a nucleic acid sample together with wild-type nucleic acids, with high specificity and high sensitivity.

Solution to Problem

The present inventors conducted intensive studies to solve the object, and found that a clamp probe which comprises a photo-crosslinking nucleic acid and which has a sequence complementary to a target site having a wild-type nucleic acid sequence is crosslinked with a wild-type nucleic acid having the target site, to selectively inhibit amplification of the wild-type nucleic acid. That is to say, such a photo-crosslinking nucleic acid is used to specifically perform the photo-crosslinking only when a complete hybrid is formed, and to maintain the linkage (i.e., a non-equilibrium state) in any temperature cycle of a nucleic acid amplification reaction, and as a result, it can be inhibited that the target molecule functions as a template for the nucleic acid amplification reaction. This finding enabled both the high clamping (i.e., inhibition) effect of a wild-type nucleic acid and the selective (i.e., specific) nucleic acid amplification of a mutated nucleic acid.

The present invention relates to:

[1] A method for inhibiting amplification of a detection region comprising a target site, said amplification being performed by a nucleic acid amplification method, comprising the steps of:
  allowing
    a nucleic acid having a target site, and
    a clamp probe comprising a photo-crosslinking nucleic acid and having a sequence complementary to the target site
  to coexist with each other; and
  photo-crosslinking the nucleic acid having the target site with the clamp probe by photo-irradiation.

[2] A method for detecting a mutated nucleic acid, comprising the steps of:
  (a) allowing
    a clamp probe comprising a photo-crosslinking nucleic acid and having a sequence complementary to a target site having a sequence of a wild-type nucleic acid, and
    a nucleic acid sample
  to coexist with each other, and specifically forming a hybrid of the clamp probe with a wild-type nucleic acid molecule having the target site;
  (b) photo-crosslinking the hybrid-forming clamp probe/target nucleic acid molecule by photo-irradiation;
  (c) subjecting the reaction product obtained by steps (a) and (b) to a nucleic acid amplification reaction; and
  (d) analyzing the resulting amplified product,
wherein a detection region comprising a target site of the mutated nucleic acid is selectively amplified to detect the presence or absence of the mutated nucleic acid.

[3] A method for detecting a mutated nucleic acid, comprising the steps of:
  (a) allowing
    a clamp probe comprising a photo-crosslinking nucleic acid and having a sequence complementary to a target site having a sequence of a wild-type nucleic acid, and
    a nucleic acid sample
  to coexist with each other, and specifically forming a hybrid of the clamp probe with a wild-type nucleic acid molecule having the target site;
  (b) photo-crosslinking the hybrid-forming clamp probe/target nucleic acid molecule by photo-irradiation;
  (c) performing steps (a) and (b) during a nucleic acid amplification reaction; and
  (d) analyzing the resulting amplified product,
wherein a detection region comprising a target site of the mutated nucleic acid is selectively amplified to detect the presence or absence of the mutated nucleic acid.

[4] The method according to any one of [1] to [3], wherein the nucleic acid amplification reaction is a PCR method.

[5] The method according to any one of [1] to [3], wherein the nucleic acid amplification reaction is a real-time PCR method.

[6] The method according to any one of [1] to [3], wherein the clamp probe has a sequence complementary to the sense chain and/or the antisense chain of the target nucleic acid molecule.

[7] The method according to any one of [1] to [6], wherein the chain length of the clamp probe is 7 to 30 nucleotides.

[8] The method according to any one of [1] to [7], wherein the photo-irradiation is performed at a wavelength of 350 to 380 nm.

[9] The method according to any one of [1] to [8], wherein the photo-irradiation is performed one or more times, in a temperature cycle where ordinary complementary chains bind to and dissociate from each other, at a temperature where the complementary chains can bind to each other.

[10] The method according to any one of [1] to [9], wherein the photo-irradiation is performed using a nucleic acid amplification apparatus with a photo-irradiation unit at a wavelength of 350 to 380 nm.

[11] A kit for inhibiting amplification of a detection region comprising a target site, said amplification being performed by a gene amplification method, comprising:
a clamp probe comprising a photo-crosslinking nucleic acid and having a sequence complementary to the target site, and
a primer capable of amplifying the detection region comprising the target site.

[12] A kit for detecting a mutated nucleic acid, comprising:
a clamp probe comprising a photo-crosslinking nucleic acid and having a sequence complementary to a target site having a sequence of a wild-type nucleic acid, and
a primer capable of amplifying a detection region comprising a target site,
wherein a detection region comprising a target site of the mutated nucleic acid is selectively amplified to detect the presence or absence of the mutated nucleic acid.

[13] A nucleic acid amplification apparatus with a photo-irradiation unit at a wavelength of 350 to 380 nm.

[14] A nucleic acid amplification apparatus with a photo-irradiation unit at a wavelength of 350 to 380 nm, comprising the steps of:
 (a) allowing
  a clamp probe comprising a photo-crosslinking nucleic acid and having a sequence complementary to a target site, and
  a nucleic acid sample
 to coexist with each other, and specifically forming a hybrid of the clamp probe with a nucleic acid molecule having the target site;
 (b) photo-crosslinking the hybrid-forming clamp probe/target nucleic acid molecule by photo-irradiation; and
 (c) subjecting the reaction product obtained by steps (a) and (b) to a nucleic acid amplification reaction.

[15] A nucleic acid amplification apparatus with a photo-irradiation unit at a wavelength of 350 to 380 nm, comprising the steps of:
 (a) allowing
  a clamp probe comprising a photo-crosslinking nucleic acid and having a sequence complementary to a target site, and
  a nucleic acid sample
 to coexist with each other, and specifically forming a hybrid of the clamp probe with a nucleic acid molecule having the target site;
 (b) photo-crosslinking the hybrid-forming clamp probe/target nucleic acid molecule by photo-irradiation; and
 (c) performing steps (a) and (b) during a nucleic acid amplification reaction.

Advantageous Effects of Invention

According to the present invention, the presence or absence of a mutated nucleic acid which is contained in a small amount in a nucleic acid sample can be rapidly and easily detected with high specificity and high sensitivity.

DESCRIPTION OF EMBODIMENTS

Figure 1:
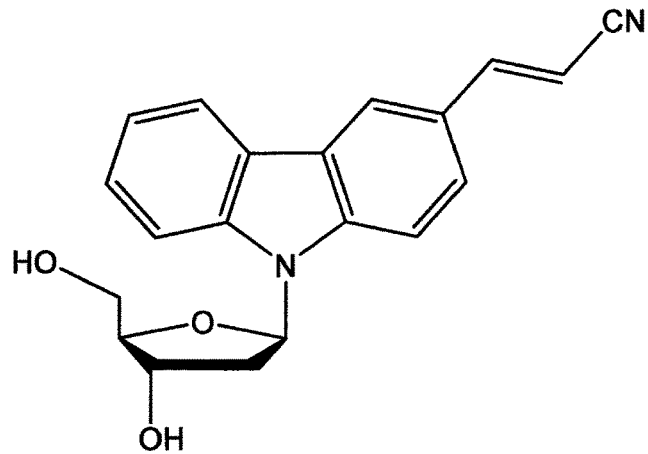
FIG. 1 is the structural formula of 3-cyanovinylcarbazole-1'-β-deoxyriboside (CNVK).

The definitions of the terms as used herein, such as DNA, RNA, nucleic acid, gene, gene expression, code, complementary, template, promoter, probe, primer, hybridization, and PCR, are the same as those currently and commonly used in molecular biology, genetics, genetic engineering, and the like.

The term "nucleic acid" as used herein is not limited, so long as it is DNA or RNA, or nucleic acid analogues described below. The nucleic acid may be a naturally-occurring compound or a synthetic compound. Examples of the naturally occurring nucleic acid include genomic DNA, mRNA, tRNA, rRNA, and hnRNA collected from organisms. Examples of the synthetic nucleic acid include DNA synthesized by a known chemical synthesis method such as a β-cyanoethylphosphoramidite method or a DNA solid-phase synthesis method, nucleic acid synthesized by a known nucleic acid amplification method such as PCR, and cDNA synthesized by a reverse-transcriptional reaction.

The term "wild-type nucleic acid" as used herein means a nucleic acid prior to mutation, typically, a nucleic acid which has no mutations and contains genetic information having its original normal functions. The term "genetic information" as used herein includes not only a transcriptional region which encodes information of mRNA, tRNA, rRNA, snRNA, and the like, but also a regulatory region such as a promoter which is required for gene expression.

The term "mutated nucleic acid" as used herein means a nucleic acid in which a mutation has occurred. The term "mutation" as used herein means a change in the sequence of a nucleic acid such as DNA and RNA, and includes a base substitution, insertion, deletion, inversion, duplication, translocation, and the like used in genetics and the like. The region of the mutation in a mutated nucleic acid is not limited to a transcriptional region, but includes a regulatory region such as a promoter which is required for gene expression. In this regard, the mutation in a mutated nucleic acid does not require a functional change. The "mutation" includes congenital and acquired mutations.

The term "target site" as used herein means a site which is a target of a clamp probe comprising a photo-crosslinking nucleic acid in a nucleic acid sequence, and which has a nucleotide sequence which hybridizes with all or part of the clamp probe.

The term "target site" as used in ordinary embodiments means a site in which a mutated base exists in a mutated nucleic acid, and a site to be detected as a target in the present invention, including a wild-type nucleic acid. For example, in the case of a base substitution, the target site is a base which is substituted in both a wild-type nucleic acid and a mutated nucleic acid. In the case of an insertion, the target site in a mutated nucleic acid is an inserted base, and the target site in a wild-type nucleic acid is a site into which the base is inserted in the mutated nucleic acid. In the case of a deletion, the target site in a mutated nucleic acid is a site in which a base is deleted by the deletion, and the target site in a wild-type nucleic acid is the deleted base in the mutated nucleic acid. The sequence of a target site may be a chain having a sequence which encodes genetic information (hereinafter referred to as a sense chain), or a chain having a sequence complementary to the sense chain (hereinafter referred to as an antisense chain).

The term "nucleic acid amplification reaction" as used herein means an amplification reaction of a template nucleic acid utilizing a known polymerase reaction. The term "nucleic acid amplification apparatus" as used herein means an apparatus by which the "nucleic acid amplification reaction" can be performed.

The method for inhibiting amplification of the present invention is a method in which, while an ordinary nucleic acid amplification method using primers capable of amplifying a detection region comprising a target site is performed, amplification of one nucleic acid (for example, a wild-type nucleic acid) is inhibited, whereas the other nucleic acid (for example, a mutated nucleic acid) is selectively amplified, based on the mutation at the target site.

In the present invention, the subject of the amplification inhibition is not limited, and either of a wild-type nucleic acid and a mutated nucleic acid may be appropriately selected as the subject in accordance with the purpose. For example, in the case where there is a significant difference in the contents in a nucleic acid sample, the presence or absence of a nucleic acid which exists in a small amount (for example, a mutated nucleic acid) can be detected by inhibiting amplification of a nucleic acid which exists in a large amount (for example, a wild-type nucleic acid) and selectively amplifying the nucleic acid which exists in a small amount.

Hereinafter the method of the present invention will be mainly explained on the basis of an embodiment of the present invention, a method for detecting a mutated nucleic acid to detect the presence or absence of the mutated nucleic acid. However, an essential feature of the method of the present invention is, as described above, to inhibit the amplification of only one nucleic acid based on the mutation at the target site, while an ordinary nucleic acid amplification method using primers capable of amplifying a detection region comprising the target site is performed.

The first embodiment of the method of the present invention is a method for detecting a mutated nucleic acid, comprising the steps of:

(a) allowing
a clamp probe comprising a photo-crosslinking nucleic acid and having a sequence complementary to a target site having a sequence of a wild-type nucleic acid, and
a nucleic acid sample
to coexist with each other, and specifically forming a hybrid of the clamp probe with a wild-type nucleic acid molecule having the target site;
(b) photo-crosslinking the hybrid-forming clamp probe/target nucleic acid molecule by photo-irradiation;
(c) subjecting the reaction product obtained by steps (a) and (b) to a nucleic acid amplification reaction; and
(d) analyzing the resulting amplified product,
wherein a detection region comprising a target site of the mutated nucleic acid is selectively amplified to detect the presence or absence of the mutated nucleic acid.

The second embodiment of the method of the present invention is a method for detecting a mutated nucleic acid, comprising the steps of:

(a) allowing
a clamp probe comprising a photo-crosslinking nucleic acid and having a sequence complementary to a target site having a sequence of a wild-type nucleic acid, and
a nucleic acid sample
to coexist with each other, and specifically forming a hybrid of the clamp probe with a wild-type nucleic acid molecule having the target site;
(b) photo-crosslinking the hybrid-forming clamp probe/target nucleic acid molecule by photo-irradiation;
(c) performing steps (a) and (b) during a nucleic acid amplification reaction; and
(d) analyzing the resulting amplified product,
wherein a detection region comprising a target site of the mutated nucleic acid is selectively amplified to detect the presence or absence of the mutated nucleic acid.

In the present invention, a mutated nucleic acid can be detected with high sensitivity by those steps, i.e., inhibiting amplification of a wild-type nucleic acid and selectively amplifying the mutated nucleic acid.

Hereinafter each step will be explained in turn. Since the first embodiment is the same as the second embodiment except for step (c), each step will be explained mainly based on the first embodiment, and then, the second embodiment will be explained with respect to the features different from those of the first embodiment.

In step (a), a clamp probe which comprises a photo-crosslinking nucleic acid and which has a sequence complementary to a target site having a sequence of a wild-type nucleic acid is allowed to coexist with a nucleic acid sample, and a hybrid of the clamp probe with a target nucleic acid molecule having the wild-type nucleic acid sequence is specifically formed. This reaction can be performed under conventional conditions suitable for hybrid formation (temperature, pH, salt concentration, buffer, and the like), and the specific hybrid formation of the clamp probe with the wild-type nucleic acid can be promoted by adding, for example, dimethyl sulfoxide (DMSO) or formamide to the reaction solution. In connection to this, it is preferable to avoid incorporation of a substance which inhibits a nucleic acid amplification reaction which is performed after or at the same time as the hybrid formation. In particular, a reaction formulation suitable for a nucleic acid amplification reaction is preferable, when the hybrid formation is performed at the same time of the nucleic acid amplification reaction.

The "nucleic acid sample" used in step (a) is not limited, so long as it is a sample containing nucleic acid and suspected of containing a nucleic acid comprising a target site. It is preferably a sample suspected of containing at least one wild-type nucleic acid having a target site and its mutated nucleic acid, and more preferably a sample suspected of containing both nucleic acids. Examples of the nucleic acid sample include RNA or genomic DNA obtained from whole cells contained in a sample such as blood or tissues. Nucleic acid can be extracted from a sample by a conventional method such as a phenol/chloroform method. In connection to this, the percentage of presence of the mutated nucleic acid in the target nucleic acids to be detected is not limited. For example, it may be 100% of a wild-type nucleic acid, or 50% of a wild-type nucleic acid and 50% of a mutated nucleic acid. The nucleic acid sample may be genomic DNA obtained from cells, mRNAs prepared from cells, or cDNAs obtained by a reverse-transcription reaction using mRNAs as a template. Further, the nucleic acid sample may be an artificial mixture of a number of cloned genes, nucleic acid artificially amplified by a nucleic acid amplification method, or a mixture thereof.

The photo-crosslinking nucleic acid which may be used in the present invention is not limited, so long as it can be crosslinked with nucleic acid at a target site or nucleic acid close to the target site by photo-crosslinking. For example, psoralen derivatives (Chang, E. et al. Biochemistry 1991, 30, 8283), aminopurine derivatives (JP 2001-206896 A), or 4-thiouracil may be used. Since the psoralen derivatives have properties that specifically react with thymine in the nucleotide sequence 5'-AT-3', and the aminopurine derivatives are not sequence-dependent, but are cytidine-specific, the application of these derivatives is limited, and therefore, the following photo-crosslinking nucleic acids without such limitations are preferable.

The first preferable photo-crosslinking nucleic acids are nucleic acids having, as the base moiety, the group of the formula I:

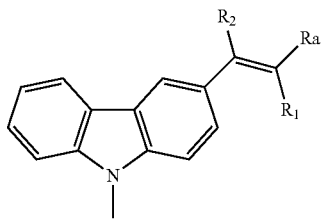

[Chem. 1]

wherein Ra is a cyano group, an amide group, a carboxyl group, a $C_2$-$C_7$ alkoxycarbonyl group, or a hydrogen atom, and $R_1$ and $R_2$ are independently a cyano group, an amide group, a carboxyl group, a $C_2$-$C_7$ alkoxycarbonyl group, or a hydrogen atom (Org. Lett., Vol. 10, No. 15, 2008, JP 2009-254279 A). In the case where a nucleic acid attached thereto is DNA, the substituted carbazolyl group of the formula I is linked to the carbon atom (C) at the 1-position of 2-deoxyribose at the β-position, as shown in the formula I(a):

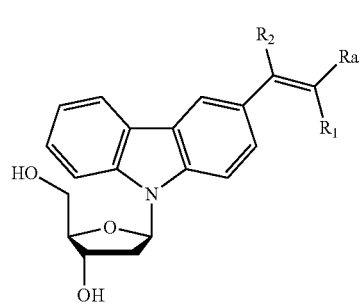

[Chem. 2]

Concrete examples of the first photo-crosslinking nucleic acids include 3-cyanovinylcarbazole-1'-β-deoxyriboside ($^{CNV}$K).

The second preferable photo-crosslinking nucleic acids are nucleic acids having the group of the formula II:

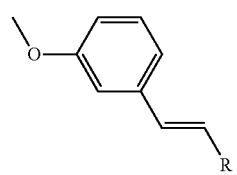

[Chem. 3]

wherein R is —CN, —CONR$^1$R$^2$, or —COOR$^3$, R$^1$ to R$^3$ are independently a hydrogen atom or an alkyl group $C_nH_{2n+1}$ (n≥1), and the upper limit of n is not limited, but may be, for example, 1 to 7, preferably 1 to 5 (Organic & Biomolecular Chemistry 2007, 5, 2583, Bioorganic & Medicinal Chemistry Letters 15 (2005) 1299-1301, and JP 2005-348645 A). In the case where a nucleic acid attached thereto is DNA, the substituted phenoxy group of the formula II is linked to the carbon atom (C) at the 1-position of 2-deoxyribose at the α-position, as shown in the formula II(a):

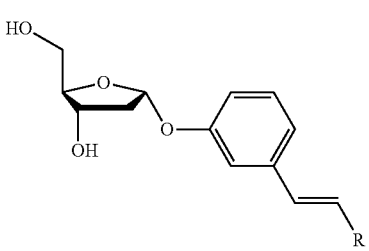

[Chem. 4]

R is preferably —CN, —COOH, or —COOMe, and more preferably —COOH or —COOMe.

The groups of the formula I and formula II impart photo-crosslinking properties to the nucleic acid. The photo-crosslinking properties may be imparted to DNA and RNA as well as nucleotide analogues. These photo-crosslinking nucleic acids may be prepared in a fashion similar to a conventional method of producing nucleic acid.

The "clamp probe" used in step (a) means a nucleic acid probe which comprises the above-mentioned photo-crosslinking nucleic acid and which has a sequence complementary to a target site. The clamp probe may contain the photo-crosslinking nucleic acid having the group of the formula I or the formula II, and the clamp probe comprising the group of the formula I is preferable. The clamp probe may be DNA and RNA as well as nucleotide analogues. The method for detecting a mutated nucleic acid of the present invention is characterized in that the photo-crosslinking nucleic acid contained in the clamp probe has the sequence complementary to a target site of a wild-type nucleic acid. The nucleotide sequence of the clamp probe, and the position and number of the photo-crosslinking nucleic acids are not limited, so long as the clamp probe can specifically hybridize with part or all of the target site. The length of the clamp probe is not limited, so long as it can specifically hybridize therewith, and is preferably, for example, 7 or 30 nucleotides.

The "nucleotide analogue" means a non-natural (i.e., artificially produced) nucleotide having the same functions as those of naturally occurring nucleotides such as deoxyribonucleotide (DNA) and ribonucleotide (RNA). That is to say, nucleotide analogues can form a chain by a phosphodiester bond, like nucleotides, and a primer or a probe prepared using nucleotide analogues can be used in PCR or hybridization, like a primer or a probe prepared using nucleotides alone. Examples of such nucleotide analogues include PNA (polyamide nucleotide derivative), LNA (BNA), and ENA (2'-O,4'-C-ethylene-bridged nucleic acids), as well as mixtures thereof. PNA is a compound in which the main chain consisting of phosphate and pentose in DNA or RNA is substituted with a polyamide chain. LNA (BNA) is a compound having two cyclic structures in which the oxygen atom at the 2'-position of the ribonucleoside is linked to the carbon atom at the 4'-position thereof via methylene.

The clamp probe used in step (a) may be prepared not only against the sense chain, but also against the antisense chain. In particular, in the case where a nucleic acid contained in a nucleic acid sample is double-stranded DNA, the effect of inhibiting nucleic acid amplification of a wild-type nucleic acid can be increased in step (c) described below, by simultaneously using both clamp probes prepared against both chains, and photo-crosslinking the clamp probes with the target sites of both chains. With respect to the clamp probes against the sense and antisense chains, it is preferable to introduce the photo-crosslinking nucleic acids into sites where the clamp probes are not photo-crosslinked with each other.

In step (b), the clamp probe and its complementary wild-type nucleic acid molecule, which form a hybrid, are subjected to photo-irradiation to photo-crosslink the clamp probe with the target nucleic acid molecule. The resulting photo-crosslinking is generated by forming an intermolecular covalent bond between the photo-crosslinking nucleic acid and the target nucleic acid molecule, due to a photo-reaction of the artificial base moiety of the photo-crosslinking nucleic acid, and corresponds to intermolecular cross-linking. Since the crosslinked molecules are not assembled by thermal stability alone, the binding is maintained without dissociation, even when the crosslinked molecules are under the conditions where complementary double-stranded chains dissociate from one another.

The photo-crosslinking reaction in step (b) may be performed in a reaction solution containing a salt with buffer action. Examples of the salt with buffer action include cacodylate, phosphate, and tris salt. The concentration of the salt with buffer action is preferably 5 to 250 mmol/L. Further, it is preferable that the reaction solution contains an alkali metal salt and/or an alkali earth metal salt. Examples of the alkali metal and/or the alkali earth metal include sodium chloride and magnesium chloride. Furthermore, the specific photo-crosslinking reaction between the clamp probe and the wild-type nucleic acid can be promoted by adding an organic solvent, such as DMSO or formamide, to the reaction solution. In connection to this, it is preferable to avoid incorporation of a substance which inhibits a nucleic acid amplification reaction which is performed after or at the same time as the photo-crosslinking. In particular, a reaction formulation suitable for a nucleic acid amplification reaction is preferable, when the photo-crosslinking is performed at the same time as the nucleic acid amplification reaction.

In the photo-irradiation of step (b), the wavelength of light is generally 350 to 380 nm, and preferably 366 nm. Laser light of a single wavelength at 366 nm is most preferable. In a preferred embodiment, the light reaction by photo-irradiation is preferably performed within one to several seconds. In connection to this, taking into consideration the optical transparency of a reaction vessel and a reaction solution, the light reaction time may be prolonged.

Since the photo-crosslinking in step (b) can maintain the binding even under the conditions where complementary double-stranded chains prepared by conventional hybrid formation dissociate from each other, as described above, a complementary wild-type nucleic acid molecule crosslinking to the clamp probe can be accumulated by repeating the photo-irradiation in a temperature cycle where ordinary complementary chains bind to and dissociate from each other, at a temperature where the complementary chains can bind together.

In the case where the nucleic acid sample used in steps (a) and (b) is RNA such as mRNA, after a photo-crosslinking reaction with the clamp probe is performed, cDNA may be synthesized and subjected to an amplification reaction such as PCR, or gene amplification may be performed by 1-step PCR or the like. Alternatively, after cDNA is synthesized, RNA may be amplified by an in vitro transcription method.

In the case where the nucleic acid sample used in steps (a) and (b) is single-stranded DNA such as cDNA, after a photo-crosslinking reaction with the clamp probe is performed, the reaction product may be subjected to an amplification reaction such as PCR, or RNA may be amplified by an in vitro transcription method.

In the case where the nucleic acid sample used in steps (a) and (b) is double-stranded DNA such as chromosomal DNA, after hybridized double-stranded DNA is treated under denaturation conditions, such as heat denaturation or acidic conditions, to convert it to single-stranded DNA, step (a) may be performed in a similar fashion to the case of single-stranded DNA.

In step (c), the nucleic acid sample which has been subjected to the photo-crosslinking reaction is used as a template, and a nucleic acid amplification method (for example, PCR) using amplification primers is performed to amplify a detection region comprising the target site. The amplification primer used in step (c) is a primer which is capable of amplifying a detection region comprising the target site of a mutated nucleic acid, and which is also capable of amplifying a detection region comprising the target site of a wild-type nucleic acid with which the clamp probe is not photo-crosslinked. Since the molecule having the wild-type sequence is crosslinked with the clamp probe by photo-irradiation, an elongation reaction from the cross-linked nucleotide to the 3' terminus does not proceed, and the molecule having the wild-type sequence is not amplified. By contrast, since almost all the molecules having the mutated sequence are not crosslinked with the clamp probe, an elongation reaction occurs, and as a result, selective nucleic acid amplification is achieved.

In the case where the nucleic acid amplification method is PCR, the amplification primers used in step (c) are primers capable of amplifying a nucleotide sequence (nucleotide sequence for amplification) comprising one target nucleotide sequence or two or more target nucleotide sequences, and two kinds of primers between which the nucleotide sequence for amplification is sandwiched. For example, the primers may be two kinds of primers consisting of a forward primer having a nucleotide sequence homologous to the upstream region of the nucleotide sequence for amplification, and a reverse primer having a nucleotide sequence complementary to the downstream region of the nucleotide sequence for amplification. The concentrations of the two primers used in PCR are not limited, so long as the concentration ratio is a value capable of obtaining double-stranded nucleic acid as a PCR product. It is preferable that the two primers are used at equal concentrations.

The primers used in PCR may be designed and synthesized in accordance with conventional methods, on the basis of the sequence information of a nucleotide sequence comprising the target nucleotide sequence.

The primers used in PCR are compounds in which one or more molecules selected from the group consisting of nucleotides and nucleotide analogues are linked by a phosphodiester bond. The length of the primer may be appropriately selected in accordance with the Tm value of the primer, the type of a nucleotide sequence to be amplified, and the like, and a primer in which 10 to 100 molecules are linked is preferable.

PCR may be performed by a conventional method, in accordance with a commonly used protocol, using commonly used amounts of commonly used reagents. DNA polymerase used in PCR is not limited, so long as it is commonly used in PCR, and a thermostable polymerase is preferable.

Since the crosslinking with a target molecule by photo-irradiation inhibits the elongation reaction by polymerase, the resistivity of the clamp probe per se against a nuclease activity is not required. Therefore, a polymerase having nuclease activity may be used. In the case where the nucleic acid which functions as a primer and causes the elongation reaction by polymerase is used for clamp probe, it is preferable that the Tm value is selected so that the nucleic acid is dissociated from the target molecule at a temperature where the elongation reaction by polymerase occurs, or that the 3' terminus of the clamp probe is modified with a substance which inhibits the elongation reaction so that the nucleic acid does not function as an amplification primer.

In step (d), examples of a method for analyzing the amplified product obtained by step (c) include the following known methods. For example, as a method using the amplified product obtained by step (c), in the case where the mutated nucleic acid contained in the amplified product has a known mutation, the presence or absence of the mutated nucleic acid can be judged using a substrate assay such as microarray. Further, when an RFLP method is used, there is a case where the presence or absence of the mutated nucleic acid can be judged by the presence or absence of digestion with a restriction enzyme. Furthermore, when it is considered that the target site contains an unknown mutated nucleic acid, the presence or absence of the mutated nucleic acid can be judged by determining the nucleotide sequence of the amplified product of the detection region.

On the other hand, for example, in the case where the mutated nucleic acid to be judged is a known mutation, the presence or absence of the mutated nucleic acid can be judged or quantified by performing a known real-time PCR in step (c). This embodiment in which step (c) and step (d) are performed at the same time is preferable, because the presence or absence of the mutated nucleic acid can be rapidly and easily judged. The method in which the amplification of the mutated nucleic acid and the judgment is performed at the same time by a real-time PCR may be performed with reference to Patent literature 1.

Next, the second embodiment will be explained based on the features different from those of the first embodiment.

A difference from the first embodiment is to perform step (a) and step (b) during the nucleic acid amplification reaction of step (c). More particularly, for example, in PCR, photo-irradiation is performed under the temperature conditions capable of forming the hybrid of the target molecule with the clamp probe (i.e., step (a)), and the target nucleic acid is linked to the photo-crosslinking nucleic acid contained in the clamp probe (i.e., step (b), to directly and selectively amplify the mutated nucleic acid.

The photo-irradiation may be performed one or more times. Since the amplification of the wild-type nucleic acid can be more completely inhibited by repeating the photo-irradiation in each amplification cycle, it is preferable to repeat the photo-irradiation in each cycle of PCR. The photo-irradiation may be performed in all amplification cycles, or the photo-irradiation may be started or ended at any amplification cycle.

The PCR reaction in step (c) may be performed using a reaction formulation suitable for a conventional PCR amplification reaction. Further, a substance which affects the hybridization conditions, such as DMSO or formamide, may be added to the reaction solution to promote the selective amplification reaction of the mutated nucleic acid.

The kit of the present invention is a kit for detecting a mutated nucleic acid, comprising:

a clamp probe comprising a photo-crosslinking nucleic acid and having a sequence complementary to a target site having a sequence of a wild-type nucleic acid, and a primer capable of amplifying a detection region comprising a target site, wherein a detection region comprising a target site of the mutated nucleic acid is selectively amplified to detect the presence or absence of the mutated nucleic acid. The kit may further contain, for example, a buffer, polymerase for amplification, and the like.

The apparatus of the present invention is a nucleic acid amplification apparatus with a photo-irradiation unit at a wavelength of 350 to 380 nm. The nucleic acid amplification apparatus is not limited, so long as it can perform each reaction in the present invention, and includes a known nucleic acid amplification unit. A real-time PCR apparatus capable of quantifying amplified nucleic acid may be preferably used. A photo-irradiation unit at a wavelength of 350 to 380 nm may be added to such an apparatus.

The apparatus of the present invention may preferably comprise
a program which can perform the following steps (a) to (c) of the first embodiment of the present invention:

(a) allowing a clamp probe comprising a photo-crosslinking nucleic acid and having a sequence complementary to a target site, and a nucleic acid sample to coexist with each other, and specifically forming a hybrid of the clamp probe with a nucleic acid molecule having the target site;

(b) photo-crosslinking the hybrid-forming clamp probe/target nucleic acid molecule by photo-irradiation; and (c) subjecting the reaction product obtained by steps (a) and (b) to a nucleic acid amplification reaction, and/or, a program which can perform the following steps (a) to (c) of the second embodiment of the present invention:

(a) allowing a clamp probe comprising a photo-crosslinking nucleic acid and having a sequence complementary to a target site, and a nucleic acid sample to coexist with each other, and specifically forming a hybrid of the clamp probe with a nucleic acid molecule having the target site;

(b) photo-crosslinking the hybrid-forming clamp probe/target nucleic acid molecule by photo-irradiation; and (c) performing steps (a) and (b) during a nucleic acid amplification reaction.

EXAMPLES

The present invention now will be further illustrated by, but is by no means limited to, the following Examples.

Example 1

Evaluation of Inhibition of PCR Amplification with Respect to Wild-Type Gene
(Materials and Methods)
1. Preparation of Photo-Crosslinking Clamp Probes Mutation points Gly12 and Gly13 on a KRAS gene were selected as the target site, and a clamp probe complementary to the sense chain capable of hybridizing with the target site having the wild-type sequence was designed. Similarly, a clamp probe against the antisense chain was designed. A photo-crosslinking nucleic acid, 3-cyanovinylcarbazole-1'-β-deoxyriboside (CNVK) (Prepared by a method described in JP 2009-254279 A. Obtained from Fujimoto lab., School of Materials Science, Japan Advanced Institute of Science and Technology), was introduced to the clamp probes at the sites where the clamp probes were not photo-crosslinked with each other. The synthesis of the clamp probes was entrusted to FASMAC Co., Ltd. The sequences of the clamp probes are shown in Table 1. The structural formula of CNVK is shown in FIG. 1.

TABLE 1

| Clamp probe | Sequence | Remarks |
|---|---|---|
| ODN09 | GCCTA$^{CNV}$KGCCACCAGC | Complementary to sense chain of wild-type KRAS sequence |
| ODN10 | TTGGA$^{CNV}$KCTGGTGGCG | Complementary to antisense chain of wild-type KRAS sequence |

2. Preparation of Wild-Type KRAS Gene Fragment

Human genomic DNA was prepared from peripheral blood of a healthy person by a conventional method. The resulting DNA was used as a template to amplify a KRAS exon 2 region comprising the mutation points Gly12 and Gly13, using primers F1 and R1, under conventional PCR reaction conditions. The primer sequences used in the PCR reaction are as follows:

```
                                    (SEQ ID NO: 1)
F1: 5'-AAAGGTACTGGTGGAGTATTTG-3'

(SEQ ID NO: 2)
R1: 5'-TGAAAATGGTCAGAGAAACC-3'
```

The resulting PCR amplified product was cloned by inserting it into pGEMT easy Vector (Promega KK) in accordance with the protocol attached thereto. Hereinafter, this was used as the wild-type plasmid. This plasmid was used as a template to perform amplification using the primer set of F1 and R1 under conventional PCR reaction conditions, to obtain a linear wild-type KRAS gene fragment. The resulting DNA fragment was purified using a PCR Purification Kit (Qiagen), and was used as a template in the following experiments.

3. Photo-Crosslinking Reaction of Clamp Probes with Wild-Type KRAS Gene Fragment To 1.5 mL tubes, 2 μL of 1 nmol/L wild-type KRAS gene fragment, 2 μL of 10 μmol/L clamp probe for wild-type sense chain (ODN09), and 2 μL of 10 μmol/L clamp probe for wild-type antisense chain (ODN10) were added, and adjusted to a total volume of 20 μL, at a final concentration of 1×PCR buffer (10 mmol/L Tris-HCl (pH 8.3), 50 mmol/L KCl, 1.5 mmol/L MgCl$_2$, and 0.001% (W/V) gelatin). In addition, another tubes in which both ODNs were not added and their volumes were replaced with sterile water were provided. Each tube was subjected to heat treatment on a heat block kept at 95° C. for 3 minutes, allowed to stand on a heat block kept at 55° C. for 3 minutes, and irradiated with UV-LED at 366 nm for 5 seconds. As a control, a sample not irradiated with light at 366 nm was provided.

4. Confirmation of PCR Amplification Reaction Using LightCycler

To 20 μL of each preparation obtained above, 80 μL of sterile water was added and well mixed, and 5 μL of an aliquot from each mixture was used as a template to perform a PCR reaction using primers NF1 and NR1 as well as a LightCycler (Roche). LightCycler Fast Start DNA Master SYBER Green I (Roche) was used as a PCR reaction reagent. The primer sequences are as follows:

```
                                        (SEQ ID NO: 3)
NF1: 5'-AACCTTATGTGTGACATGTTCTAA-3'

(SEQ ID NO: 4)
NR1: 5'-GTCCTGCACCAGTAATATGC-3'
```

(Results and Discussion)

Figure 2:
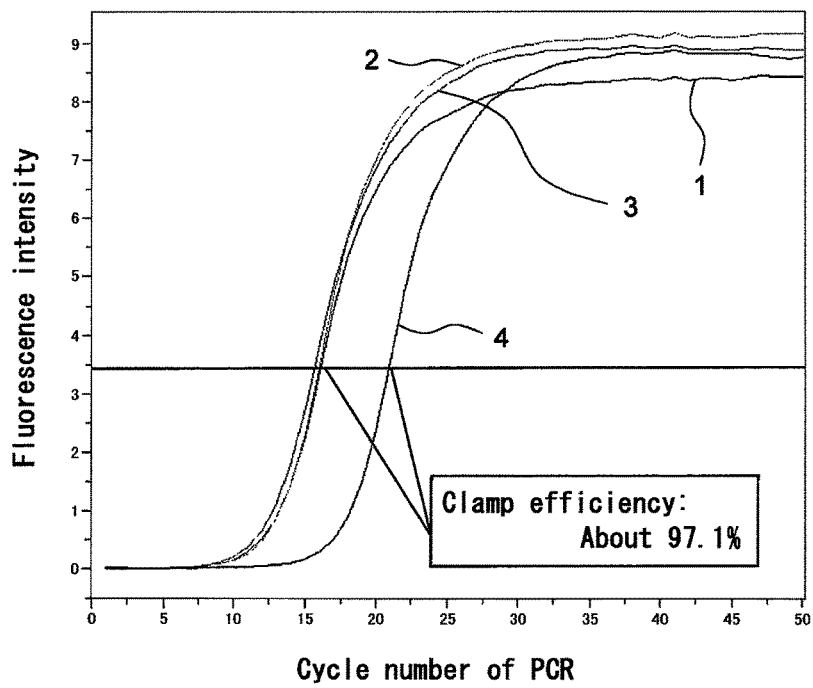
FIG. 2 is a graph showing the results of confirming, using a LightCycler, the presence or absence of inhibition of PCR amplification of a wild-type gene by photo-crosslinking reaction in Example 1.

The results are shown in FIG. 2. The vertical axis of the graph indicates fluorescence intensity, and the horizontal axis indicates the cycle number of PCR.

In comparison of the amplification curve of template sample (4) in which the ODNs were added and photo-irradiation was performed with that of template sample (3) in which the ODNs were added but photo-irradiation was not performed, the CP (crossing) value of the template sample irradiated with light increased. With respect to the amplification curves of the template samples without the addition of the ODNs, the comparison of template sample (2) with photo-irradiation to template sample (1) without photo-irradiation shows that the CP values of both were about the same. With respect to the amplification curves of the template samples without the photo-irradiation, the comparison of template sample (3) with the addition of the ODNs to template sample (1) without the addition of ODNs shows that the CP values of both were about the same. It was found from these results that the gene amplification reaction by PCR was not inhibited by performing only either of the addition of the ODNs or photo-irradiation at 366 nm, and that the clamp was formed only by performing photo-irradiation at 366 nm in the presence of the ODNs, and as a result, the amplification of the KRAS gene fragment was inhibited. Further, since the gene amplification could be inhibited by forming the clamp against the template molecule before the PCR reaction, it was confirmed that the ODNs which had been once linked with the template molecule did not dissociate from each other (i.e., a non-equilibrium state), even under the temperature conditions where ordinary hybrid formation dissociated from each other. In addition, it could be estimated from a relative comparison of the CP values that approximately 97% of the original amount of the template was photo-crosslinked with the ODNs by the photo-crosslinking reaction.

Example 2

Evaluation of Inhibition of PCR Amplification with Respect to Mutated Gene
(Materials and Methods)
1. Preparation of Mutated KRAS Gene Fragment The mutation of Gly12Ser was introduced, using Prime-STAR (registered trademark) Mutagenesis Basal Kit (Takara-Bio), into the wild-type plasmid prepared in Example 1. That is to say, the 34th base "G" of the Kras gene was changed to "A" by the method. Hereinafter, this was used as the mutated plasmid. This plasmid was used as a template to perform amplification using the primer set of F1 and R1 described in Example 1-2 under conventional PCR reaction conditions, to obtain a linear Kras mutated gene fragment. The resulting DNA fragment was purified using a PCR Purification Kit (Qiagen), and was used as a template in the following experiments.

2. Photo-Crosslinking Reaction of Clamp Probes with Mutated KRAS Gene Fragment

To 1.5 mL tubes, 2 µL of 1 nmol/L mutated KRAS gene fragment, 2 µL of 10 µmol/L ODN09, and 2 µL of 10 µmol/L ODN10 were added, and adjusted to a total volume of 20 µL, at a final concentration of 1×PCR buffer. The sequences of the clamp probes were the same as those described in Example 1. The photo-crosslinking reaction was performed under the same conditions as those described in Example 1-3. As a control, a sample not irradiated with light at 366 nm was provided.

3. Confirmation of PCR Amplification Reaction Using LightCycler

The PCR amplification reaction was performed in a fashion similar to that described in Example 1-4.
(Results and Discussion)

Figure 3:
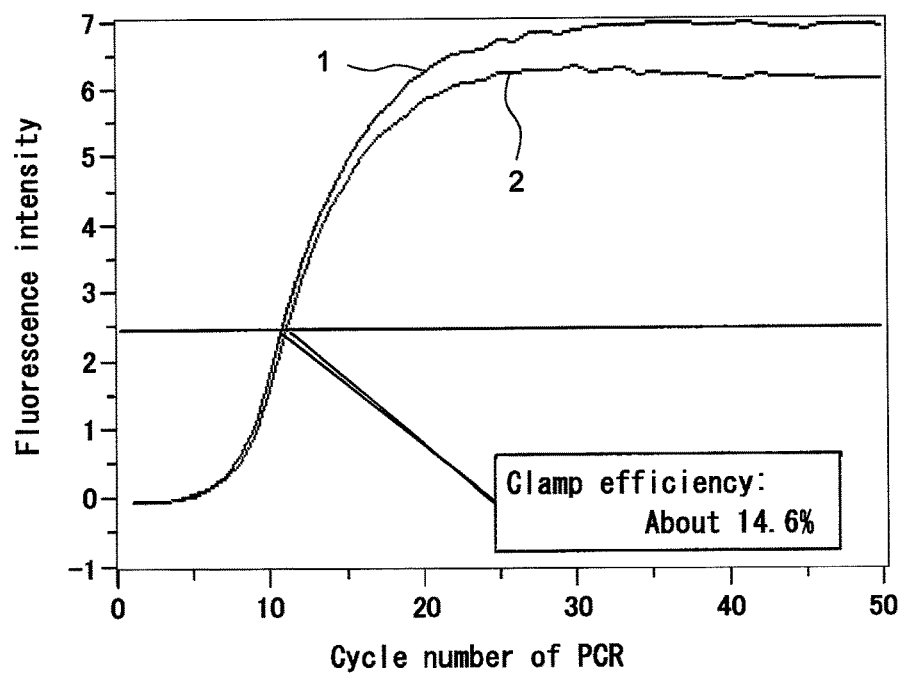
FIG. 3 is a graph showing the results of confirming, using a LightCycler, the presence or absence of inhibition of PCR amplification of a mutated gene by photo-crosslinking reaction in Example 2.

The results are shown in FIG. 3. The vertical axis of the graph indicates fluorescence intensity, and the horizontal axis indicates the cycle number of PCR.

The CP values of the sample photo-irradiated in the presence of the ODNs and the sample not photo-irradiated in the presence of the ODNs were about the same, and little inhibition of PCR amplification was observed. Since almost all the ODNs for the wild-type sequence were not photo-crosslinked with the mutated gene fragment, it was suggested that the mutated gene fragment could be selectively amplified.

Example 3

Confirmation of Selective Amplification of Mutated Nucleic Acid
(Materials and Methods)
1. Preparation of KRAS Wild-Type and Mutated Mixture Sample The KRAS wild-type and mutated gene fragments respectively prepared in Examples 1 and 2 were mixed at a ratio of 99:1 to prepare a $10^7$ copies/µL KRAS gene mixture sample.

2. Photo-Crosslinking Reaction with Clamp Probes

To 1.5 mL tubes, 2 µL of the mixture sample prepared, as well as 2 µL of 10 µmol/L ODN09 and 2 µL of 10 µmol/L ODN10 as clamp probes, were added, and adjusted to a total volume of 20 µL, at a final concentration of 1×PCR buffer. The sequences of the clamp probes were the same as those described in Example 1. The photo-crosslinking reaction was performed under the same conditions as those described in Example 1-3.

3. PCR after Photo-Crosslinking Reaction, and Cloning of PCR Product

To 20 µL of each photo-crosslinking reaction liquid obtained above, 80 µL of sterile water was added, and 5 µL of an aliquot from each mixture was used as a template to perform a PCR reaction (35 cycles) using primers NF1 and NR1 described in Example 1-4 under conventional PCR conditions. The PCR product was cloned by inserting it into pGEMT easy Vector (Promega KK) in accordance with the protocol attached thereto. HB101 competent cells (Takara-Bio) were transformed with the resulting plasmid, and cultivated on LB ampicillin plates overnight to form E. coli colonies.

4. Confirmation of Wild-Type/Mutated-Type Mixture Ratio by Sequencing

A PCR reaction was performed, using 100 colonies as templates as well as primers M13F and M13R utilizing the vector sequence, under conventional PCR conditions. These PCR products were used as templates to determine the nucleotide sequence of each clone by a direct sequencing method. The primers used in the sequencing reaction were SP6 and T7, and BigDye Terminator V1.1 cycle sequence Kit (Applied BioSystems) was used as a sequencing reaction reagent.

The primer sequences are shown below:

```
                                    (SEQ ID NO: 5)
    M13F:    5'-CAGGGTTTTCCCAGTCACGA-3'

(SEQ ID NO: 6)
    M13R:    5'-TCACACAGGAAACAGCTATG-3'

(SEQ ID NO: 7)
    SP6:     5'-ATTTAGGTGACACTATAGAA-3'

(SEQ ID NO: 8)
    T7:      5'-AATACGACTCACTATAGGG-3'
```

(Results and Discussion)

With respect to the sample with a mixture ratio (wild-type/mutated) of 99/1 before the photo-irradiation, it was confirmed that the mixture ratio increased to 87/13 after the photo-irradiation.

Example 4

Confirmation of Selective Amplification of Mutated Gene in Case of Performing Photo-Crosslinking in PCR Amplification Reaction
(Materials and Methods)
1. Preparation of PCR Reaction Solution The following reaction solution for PCR was prepared and used as a reaction solution for gene amplification:
PCR buffer (10 mmol/L Tris-HCl (pH 8.3), 50 mmol/L KCl, 1.5 mmol/L MgCl$_2$, and 0.001% (W/V) gelatin);
200 µmol/L each dNTP (=dATP, dTTP, dCTP, and dGTP); and 0.75 U/µL AmpliTaq Gold (Applied Biosystems).

To the reaction solution for gene amplification, 0.2 µmol/L NF1 and 0.2 µmol/L NR1 were added as amplification primers. Further, 0.4 µmol/L ODN09 and 0.4 µmol/L ODN10 were added as clamp probes. The sequences of the amplification primers and the clamp probes were the same as those described in Example 1. The resulting reaction solution for gene amplification was poured into discrete tubes, and 1 µL of 100 pmol/L wild-type KRAS gene fragment and 1 µL of 100 pmol/L mutated KRAS gene fragment were separately added as each template to the discrete tubes to use the following PCR reaction. Each gene fragment used as templates of this reaction corresponded to $10^7$ copies.

2. Implementation of PCR Reaction with Photo-Crosslinking Reaction

The reaction solution and each template gene fragment were added to 0.2 mL tubes for PCR as described above, and PCR was performed. The PCR reaction was performed by heating at 94° C. for 10 minutes, repeating a cycle composed of reactions at 94° C. for 30 seconds, at 55° C. for 30 seconds, and at 72° C. for 30 seconds 35 times, and heating at 72° C. for 3 minutes. In all 35 cycles, the tubes were irradiated with light at 366 nm for 5 seconds, using UV-LED, at every annealing step at 55° C. for 30 seconds to form the clamp. Both reaction solutions after PCR were subjected to electrophoresis using a 3% agarose gel, and the gel was stained with ethidium bromide to confirm amplified products using a transilluminator.

(Results and Discussion)

Figure 4:
FIG. 4 is a photograph showing the results of confirming, by agarose gel electrophoresis, the presence or absence of selective amplification of a mutated gene in the case that a photo-crosslinking reaction was performed during a PCR amplification reaction in Example 4. Lane 1 is a marker (φX174 HaeIII digest), lane 2 is the wild-type, and lane 3 is the mutated-type.

The results are shown in FIG. 4. No PCR amplified product derived from the wild-type gene fragment was detected by ethidium bromide staining after electrophoresis, whereas a PCR amplified product derived from the mutated gene fragment was detected. It was found from the results that the photo-crosslinking reaction with the clamp probes for wild-type could recognize a slight mutation such as one-base substitution, and it caused a difference in the amount of nucleic acid amplified by PCR between the wild-type and mutated sequences. It is considered that a method for selectively detecting a mutated nucleic acid with high sensitivity can be established by utilizing such clamp probes with high specificity.

Example 5

Confirmation of Detection Sensitivity of Mutated Gene in Case of Performing Photo-Crosslinking in PCR Amplification Reaction (Materials and Methods)

1. Preparation of Photo-Crosslinking Clamp Probes

Mutation point Leu858 on a EGFR gene was selected as the target site, and a clamp probe complementary to the sense chain capable of hybridizing with the target site having the wild-type sequence was designed. Similarly, a clamp probe against the antisense chain was designed. The photo-crosslinking nucleic acid described in Example 1, CNVK, was introduced to the clamp probes at the sites where the clamp probes were not photo-crosslinked with each other. The synthesis of the clamp probes was entrusted to FAS-MAC Co., Ltd. The sequences of the clamp probes are shown in Table 2.

TABLE 2

| Clamp probeSequence | Remarks |
| --- | --- |
| ODN11CA$^{CNV}$KTTTGGCCAGCCC | Complementary to sense chain of wild-type EGFR sequence |
| ODN12GA$^{CNV}$KTTTGGGCTGGCCA | Complementary to antisense chain of wild-type EGFR sequence |

2. Preparation of Wild-Type and Mutated Gene Fragments in EGFR Exon 21 Region

Human genomic DNA was prepared from peripheral blood of a healthy person by a conventional method. The resulting DNA was used as a template to amplify an EGFR exon 21 region comprising the mutation point Leu858, using primers EGFR exon 21F and EGFR exon 21R, under conventional PCR reaction conditions. The primer sequences used in the PCR reaction are as follows:

(SEQ ID NO: 9)
EGFR exon21F: 5'-GCATGAACTACTTGGAGGAC-3'

(SEQ ID NO: 10)
EGFR exon21R: 5'-ACCTAAAGCCACCTCCTTAC-3'

The resulting PCR amplified product was cloned by inserting it into pGEMT easy Vector (Promega KK) in accordance with the protocol attached thereto. Hereinafter, this was used as the wild-type plasmid. Next, the mutation of Leu858Arg was introduced, using PrimeSTAR (registered trademark) Mutagenesis Basal Kit (Takara-Bio), into the wild-type plasmid. That is to say, the 2573rd base "T" of the EGFR gene was changed to "G" by the method. Hereinafter, this was used as the mutated plasmid.

These plasmids were used as templates to perform amplification using the primer set of EGFR exon 21F and EGFR exon 21R described above under conventional PCR reaction conditions, to obtain linear wild-type and mutated gene fragments of EGFR exon 21. The resulting DNA fragments were purified using PCR Purification Kit (Qiagen).

The percentages by weight of the purified wild-type and mutated gene fragments of EGFR exon 21 were determined using NanoDrop spectrophotometer (Thermo Scientific), and taking into consideration the length of each fragment amplified, the copy number of each gene fragment was calculated. The wild-type and mutated gene fragments were mixed as shown in Table 3, and these samples were used as templates in the following experiments.

TABLE 3

| Wild-type/mutated | Sample a | Sample b | Sample c |
| --- | --- | --- | --- |
| Amounts mixed (copy number/4 μL) | $10^6/10^4$ | $10^6/10^3$ | $10^6/0$ |
| Mixture ratio | 100:1 | 1000:1 | 1:0 |

3. Amplification Reaction by PCR with Photo-Crosslinking Reaction

The reaction solution for gene amplification having the same formulation as that described in Example 4 was prepared. To this reaction solution, 0.2 μmol/L EGFR exon 21NF and 0.2 μmol/L EGFR exon 21NR were added as amplification primers. These primer sequences were as follows:

(SEQ ID NO: 11)
EGFR exon 21NF: 5'-CTTGGAGGACCGTCGCTTG-3'

(SEQ ID NO: 12)
EGFR exon 21NR: 5'-CCACCTCCTTACTTTGCCTC-3'

Further, 0.4 μmol/L ODN11 and 0.4 μmol/L ODN12 were added as clamp probes to the reaction solution for gene amplification.

To 0.2 mL tubes for PCR, 4 μL of each template gene fragment mixture with different mixture ratios was separately added, and the reaction solution for gene amplification was further added, and PCR was performed. The PCR reaction was performed by heating at 94° C. for 10 minutes, repeating a cycle composed of reactions at 94° C. for 30 seconds, at 55° C. for 30 seconds, and at 72° C. for 30 seconds 35 times, and heating at 72° C. for 3 minutes. In all 35 cycles, the tubes were irradiated with light at 366 nm for 5 seconds, using UV-LED, at every annealing step at 55° C. for 30 seconds. As controls, samples not irradiated with light at 366 nm were provided.

4. Confirmation of Copy Number by PCR Reaction Using LightCycler

Aliquots of the resulting PCR amplified products obtained in Example 5-3 were poured into tubes and diluted with sterile water to prepare 100-fold to 100,000-fold diluted samples. A PCR reaction was performed using 5 μL of each sample as a template and primers EGFR exon 21NF and EGFR exon 21NR, as well as a LightCycler (Roche). In connection to this, diluted-series (copy number=$10^3$ to $10^8$) of the wild-type gene fragment were provided as standard, and subjected to the PCR reaction at the same time. Light-Cycler Fast Start DNA Master SYBER Green I (Roche) was used as a PCR reaction reagent.

After the PCR reaction, a calibration curve was prepared from the amplification curve of the standard, and the copy number of each original sample solution was calculated from the CP value of each sample. Based on the resulting values, each PCR amplified product obtained in Example 5-3 was diluted with sterile water to $10^6$ copies/4 μL.

5. Preparation of Reaction Solution for Real-Time Quantitative PCR

A reaction solution for real-time quantitative PCR was prepared by mixing the following reagents. More particularly, 5 pmol of EGFR exon 21NF and 5 pmol of EGFR exon 21NR were added as amplification primers to 12.5 μL of 2× Premix Ex Taq (registered trademark) (Takara-Bio), and 2.5 pmol of mutation-detection probe, of which the terminal was fluorescent-labeled, was further added. The sequence of the mutation-detection probe is as follows:

L858R-detection probe: 5'-(6-FAM)tttggccCgcccaa (BHQ1)-3' The lowercase letters in the sequence represent DNA, the uppercase letter C represents LNA, 6-FAM is a fluorescent dye, and BHQ1 is a quencher, respectively. The synthesis of the mutation-detection probe was entrusted to IDT. The above volumes and amounts of the reaction solution were amounts per sample, and an amount required of the reaction solution was prepared.

6. Preparation of Reaction Solution for PNA-LNA Clamp PCR

To the reaction solution for real-time quantitative PCR prepared in Example 5-5, 12.5 pmol of PNA (L858c) was added as the clamp probe for L858R to prepare a reaction solution for PNA-LNA clamp PCR. The sequence of PNA (L858c) is as follows:

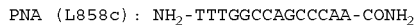

PNA (L858c): $NH_2$-TTTGGCCAGCCCAA-$CONH_2$

The synthesis of PNA (L858c) was entrusted to Panagene. The above volume of the reaction solution was an amount per sample, and an amount required of reaction solution was prepared.

7. Confirmation of Detection Sensitivity of Mutated Gene by Real-Time Quantitative PCR The PCR amplified products irradiated with light at 366 nm in Example 5-3 were diluted, with the reaction solution for real-time quantitative PCR prepared in Example 5-5, to $10^6$ copies/4 μL in accordance with the method described in Example 5-4, and 4 μL of each dilution was separately added as templates to wells. Sterile distilled water was added to the wells so as to become 25 μL as the final volume, and real-time quantitative PCR was performed using a LightCycler LC480 (Roche). As controls, the PCR amplified products not irradiated with light at 366 nm in Example 5-3 were diluted to $10^6$ copies/4 μL in accordance with the method described in Example 5-4, and real-time quantitative PCR was performed.

As comparative Examples, the PCR amplified products not irradiated with light at 366 nm in Example 5-3 were diluted, with the reaction solution for PNA-LNA clamp PCR prepared in Example 5-6, to $10^6$ copies/4 μL in accordance with the method described in Example 5-4, and 4 μL of each dilution was separately added as templates to wells. Sterile distilled water was added to the wells so as to become 25 μL as the final volume, and real-time quantitative PCR was performed at the same time. The PCR was performed by heating at 95° C. for 10 seconds, and repeating a cycle composed of reactions at 95° C. for 3 seconds and at 56° C. for 30 seconds 45 times.

(Results and Discussion)

Figure 5:
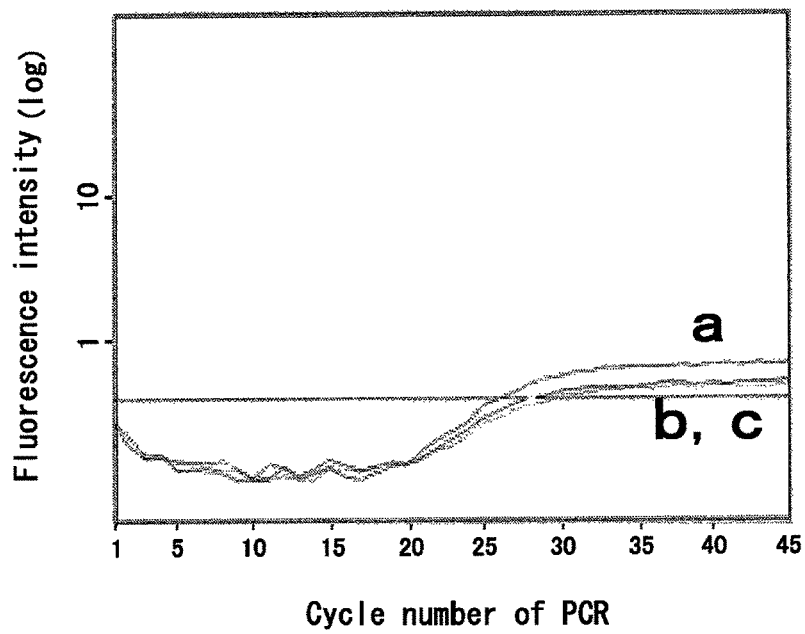
FIG. 5 is a graph showing the results of confirming, using a LightCycler, the detection sensitivity of a mutated gene in the case that a photo-crosslinking reaction was not performed during a PCR amplification reaction (control) in Example 5.
Figure 6:
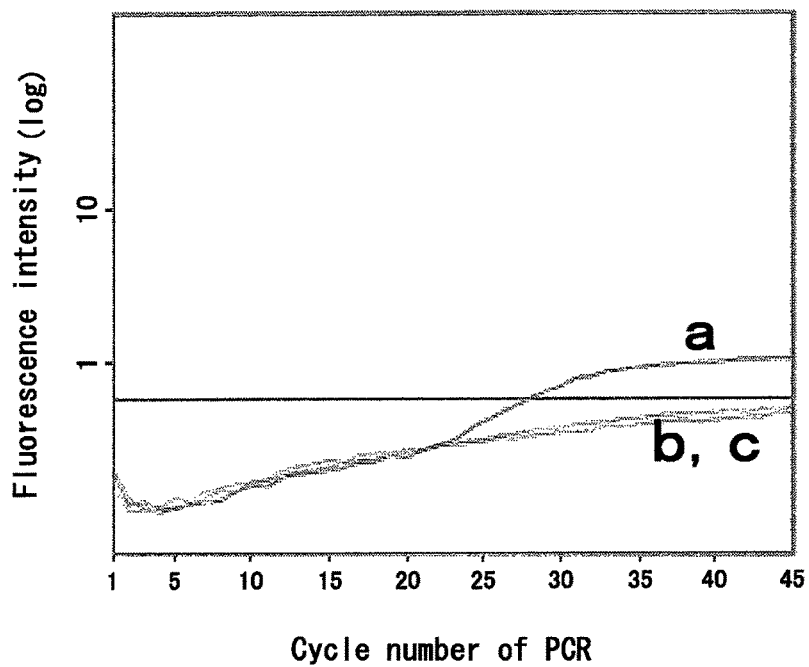
FIG. 6 is a graph showing the results of confirming, using a LightCycler, the detection sensitivity of a mutated gene by a PNA-LNA clamp PCR reaction (without a photo-crosslinking reaction during the PCR amplification reaction) (Comparative Example) in Example 5.
Figure 7:
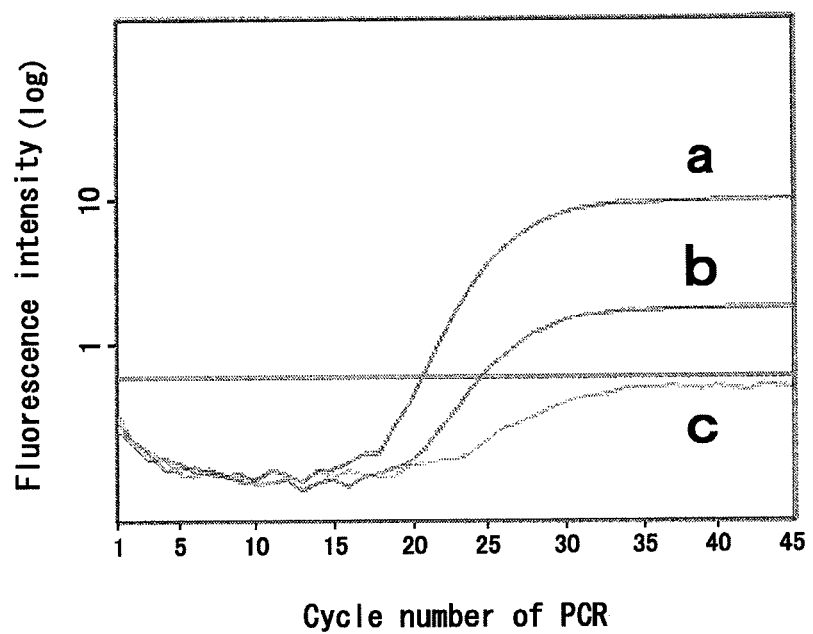
FIG. 7 is a graph showing the results of confirming, using a LightCycler, the detection sensitivity of a mutated gene in the case that a photo-crosslinking reaction was performed during a PCR amplification reaction in Example 5.

The results are shown in FIGS. 5 to 7. The vertical axis of each graph indicates fluorescence intensity, and the horizontal axis indicates the cycle number of PCR. FIG. 5 shows the results of the samples in which the photo-crosslinking reaction was not performed during the PCR amplification reaction (control). FIG. 6 shows the results of the samples in which the PNA-LNA clamp PCR reaction was performed with respect to the control samples (i.e., the samples in which the photo-crosslinking reaction was not performed during the PCR amplification reaction) (Comparative Example). FIG. 7 shows the results of the samples in which the cross-linking reaction was performed (the present invention). Symbols "a" to "c" indicate the mixture ratios of the wild-type and mutated genes used as templates in each PCR reaction. Symbol "a" is 100:1, "b" is 1000:1, and "c" is the wild-type gene alone. As shown in FIG. 5, in the samples in which the photo-crosslinking reaction and the PNA-LNA clamp PCR reaction were not performed, even when the amount of the mutated gene mixed was 1/100 (a), little difference with the signal (background) of the wild-type gene alone (c) was observed, and the mutated gene could not be detected. In the sample in which the PNA-LNA clamp PCR reaction was performed, when the amount of the mutated gene mixed was 1/100 (a), the signal could be detected, but when the amount was 1/1000 (b), no difference with the signal of the wild-type gene alone (c) was observed. That is to say, the detection sensitivity of the mutated gene was 1%. On the other hand, in the samples in which the photo-crosslinking reaction was performed with light at 366 nm (FIG. 7), even when the amount of the mutated gene mixed was 1/1000 (d), sufficient signal could be detected, and the detection sensitivity of 0.1% was confirmed.

It was revealed from the above results that, according to the present invention utilizing the photo-crosslinking reaction, the mutated EGFR gene including point mutation contained in a gene pool could be detected, even if the mixture ratio was 0.1%. Taking into consideration the facts that the limitation of reliable detection sensitivity was approximately 10% in a conventional method such as Southern blotting or direct sequencing, and that the limitation of detection sensitivity of the mutation was 1% in the PNA-LNA clamp PCR method, which was performed as Comparative Examples, the method for detecting a mutated gene of the present invention has extremely high detection sensitivity.

In the PNA-LNA clamp PCR method, the detection sensitivity of mutation is improved by utilizing a competition effect between PNA (clamp probe) and LNA (mutation detection probe). That is, the clamp formation and the detection reaction proceed at the same time. When the photo-crosslinking reaction is utilized, the clamp formation and the detection reaction can be independently performed, as shown in the Examples, mutation can be detected with high sensitivity even by a conventional real-time quantitative PCR not utilizing such a competition effect. It is considered that this fact can be achieved by allowing the binding of the photo-crosslinking clamp probe with the template molecule to be in a non-equilibrium state, and it shows the superiority of the present invention.

INDUSTRIAL APPLICABILITY

According to the present invention, a small amount of mutated gene which is contained in wild-type genes can be detected with high specificity and high sensitivity. The present invention enables early detection of cancer, or a personalized therapy by evaluating drug efficacy, by targeting a known mutation recognized as the cause of cancer, or a known mutation in which the relation with drug efficacy has been suggested. The present invention enables a detection from a blood sample or the like which is collected from a cancer patient and contains a small amount of mutated nucleic acid molecule. The present invention enables the confirmation of treatment effects, or monitoring testing, which had actually been difficult because only highly invasive specimens, such as biopsy samples or cancer tissues collected by surgery, can be handled by a conventional method, and the present invention is industrially useful.

Although the present invention has been described with reference to specific embodiments, various changes and modifications obvious to those skilled in the art are possible without departing from the scope of the appended claims.

FREE TEXT IN SEQUENCE LISTING

The nucleotide sequences of SEQ ID NOS: 5 to 8 of the sequence listing are primer sequences.

The invention claimed is:

1. A method for detecting a mutated nucleic acid, comprising the steps of:
   (a) providing
      a clamp probe comprising a photo-crosslinking nucleic acid and having a sequence complementary to a target site having a sequence of a wild-type nucleic acid, and
      a nucleic acid sample, in which a mutated nucleic acid to be detected and its wild-type nucleic acid coexist, wherein the content ratio of the mutated nucleic acid to the wild-type gene is 1/100 to 1/1000 (mutated/wild-type); and
      bringing the clamp probe into contact with the nucleic acid sample to specifically form a hybrid of the clamp probe with a wild-type nucleic acid molecule having the target site;
   (b) photo-irradiating the hybrid-forming clamp probe/target nucleic acid molecule to form a photo-crossed linked clamp probe/target nucleic acid molecule;
   (c) subjecting the reaction product obtained by steps (a) and (b) to a nucleic acid amplification reaction; and
   (d) analyzing the resulting amplified product,
   to detect the presence or absence of the mutated nucleic acid with high specificity and high sensitivity, wherein the sensitivity of detecting the mutated nucleic acid in the presence of the wild-type nucleic acid is at least 0.1%.

2. The method according to claim 1, wherein the nucleic acid amplification reaction is a PCR method.

3. The method according to claim 1, wherein the nucleic acid amplification reaction is a real-time PCR method.

4. The method according to claim 1, wherein the clamp probe has a sequence complementary to the sense chain and/or the antisense chain of the target nucleic acid molecule.

5. The method according to claim 1, wherein the chain length of the clamp probe is 7 to 30 nucleotides.

6. The method according to claim 1, wherein the photo-irradiation is performed at a wavelength of 350 to 380 nm.

7. The method according to claim 1, wherein the photo-irradiation is performed one or more times, in a temperature cycle where complementary chains bind to and dissociate from each other, at a temperature where the complementary chains can bind to each other.

8. The method according to claim 1, wherein the photo-irradiation is performed using a nucleic acid amplification apparatus with a photo-irradiation unit at a wavelength of 350 to 380 nm.

* * * * *